US009110171B2

(12) United States Patent
Nalcioglu et al.

(10) Patent No.: US 9,110,171 B2
(45) Date of Patent: Aug. 18, 2015

(54) MULTIMODALITY NUCLEAR IMAGING RECONSTRUCTION METHOD

(75) Inventors: Orhan Nalcioglu, Newport Coast, CA (US); Werner Roeck, Irvine, CA (US); Keum Sil Lee, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 74 days.

(21) Appl. No.: 13/339,174

(22) Filed: Dec. 28, 2011

(65) Prior Publication Data

US 2012/0172709 A1    Jul. 5, 2012

Related U.S. Application Data

(60) Provisional application No. 61/429,385, filed on Jan. 3, 2011.

(51) Int. Cl.
| A61B 5/055 | (2006.01) |
| G01T 1/16 | (2006.01) |
| A61B 6/00 | (2006.01) |
| G01R 33/48 | (2006.01) |
| A61B 6/03 | (2006.01) |

(52) U.S. Cl.
CPC ............. *G01T 1/1603* (2013.01); *A61B 6/5247* (2013.01); *G01R 33/481* (2013.01); *A61B 5/055* (2013.01); *A61B 6/037* (2013.01)

(58) Field of Classification Search
CPC ............................ G01R 33/481; A61B 6/5247
USPC .............. 600/411, 436; 324/318; 250/363.04, 250/363.1
See application file for complete search history.

(56) References Cited

U.S. PATENT DOCUMENTS

| 8,237,441 | B2 * | 8/2012 | Martinez-Moller et al. .. 324/318 |
| 2006/0237652 | A1 * | 10/2006 | Kimchy et al. .......... 250/363.02 |
| 2008/0029704 | A1 * | 2/2008 | Hefetz et al. ............. 250/363.01 |
| 2008/0111081 | A1 * | 5/2008 | Chuang .................... 250/363.03 |

* cited by examiner

*Primary Examiner* — Jonathan Cwern
(74) *Attorney, Agent, or Firm* — Knobbe Martens Olson & Bear LLP

(57) ABSTRACT

A method for obtaining a high-resolution nuclear image of a biological object, which image is acquired by a nuclear detector inside an MRI system includes the steps of acquiring MRI information pertaining to a wide field of view; focusing a field of view of the nuclear detector to a small region that covers only the target region; obtaining a nuclear image of the small region; and using a priori information included in the MRI information to eliminate image artifacts in the nuclear image. An apparatus for performing the method and a data image formed by practice of the method is also included.

16 Claims, 5 Drawing Sheets

MULTIMODALITY NUCLEAR IMAGING RECONSTRUCTION METHOD

RELATED APPLICATIONS

The present application is related to U.S. Provisional Patent Application Ser. No. 61/429,385, filed on Jan. 3, 2011, which is incorporated herein by reference and to which priority is claimed pursuant to 35 USC 119.

GOVERNMENT RIGHTS

The present invention was developed, at least in part, with government support under R01EB007219 (GTG) from the National Institute of Health. The United States Government may have rights to this invention.

BACKGROUND

1. Field of the Technology

The disclosure relates to the field of multimodality nuclear imaging and in particular to using limited-field-of-view techniques and a reconstruction algorithm to reconstruct nuclear and magnetic resonance images that are obtained simultaneously.

2. Description of the Prior Art

Nuclear imaging techniques such as single photon emission coherence tomography (SPECT) or positron emission tomography (PET) have proven to be useful molecular imaging techniques due to their higher detection sensitivity compared to CT or MRI. However, one of the major limitations of nuclear imaging techniques, such as SPECT, is the poor spatial resolution that is in the order of several millimeters when using parallel-hole collimators. The limitation could be improved by pinhole collimation and image magnification. Unfortunately this is only possible at the expense of a loss in detection sensitivity and increased imaging time to retain a good signal-to-noise ratio (SNR) in the images.

One way to increase the detection sensitivity while obtaining high spatial resolution is to use multi-pinhole collimators. A further disadvantage of increasing the image magnification is related to the necessity of using larger detectors resulting in increased system costs. One of the important aspects of systems using labeled radiotracers such as in SPECT is the fact that the imaging agent is mainly accumulated at the target organ while the other surrounding tissues represent a low frequency background with a lower uptake signal if the isotope is appropriately labeled. In such situations it may be sufficient only to image the target region known as the region of interest (ROI) with high resolution without paying much attention to the region outside as has been proposed elsewhere by the present inventors for CT.

Simultaneous multimodality nuclear and magnetic resonance imaging (MRI) can reduce the effect of inevitable motion between sets of image acquisitions for two or more different imaging which proves to be extremely useful if the information from the two modalities is to be co-registered or information from one is to be used as a priori information for the other. It also eliminates the necessity for post-image processing due to the misalignment of a set of images with another set obtained by a second device for images obtained consecutively.

A SPECT imaging system is characterized by a lower detection sensitivity compared to positron emission tomography (PET) due to its use of mechanical collimators. This becomes even more serious when single pinhole collimators are used for improving the spatial resolution by image magnification. In order to improve the sensitivity of a SPECT imaging system, a multiple pinhole collimator can be used instead of the single pinhole without losing spatial resolution if the detector size is not the limiting factor.

In quantum-limited imaging systems such as SPECT, the number of acquired photons, hence the image SNR, is related to the amount of radioisotope injected as well as the detection sensitivity of the collimator/detector system. Maximum allowable radiation dose also puts certain limitations on the amount of radioactive material that can be injected into the subject. By using a multiple pinhole collimator, the sensitivity can be increased considerably with a sufficiently large detector area and the radiation dose level can be reduced compared to single pinhole collimators. Unfortunately, according to previous studies, a pinhole collimator with more than nine pinholes designed to increase detection sensitivity would also increase the possibility of multiplexing in a SPECT system if the detector size is limited (image overlap on the detector) resulting in loss of resolution and SNR. Since detector size is directly related to the overall cost of a SPECT system one cannot indefinitely increase its size to eliminate image multiplexing.

BRIEF SUMMARY

The object of the illustrated embodiment is to use multimodality imaging is to integrate the strengths of different imaging technologies while reducing the shortcomings of an individual modality. In the embodiment described below magnetic resonance imaging (MRI) and single-photon emission computed tomography (SPECT) are combined.

In the illustrated embodiment a limited-field-of-view (LFOV) SPECT is implemented on a multi-modality MR/SPECT system that can be used to obtain simultaneous MRI and SPECT images for small animal imaging. The combined MR/SPECT system eliminates any possible misregistration between the two sets of images when MR images are used as a priori information for SPECT. In nuclear imaging the target area is usually smaller than the entire object, thus focusing the detector on the LFOV results in various advantages including the use of a smaller nuclear detector (less cost), smaller reconstruction region (faster reconstruction), and higher spatial resolution when used in conjunction with pinhole collimators with magnification. The MR/SPECT system can be used to choose a region of interest (ROI) for SPECT. A priori information obtained by the full field-of-view (FOV) MRI combined with the preliminary SPECT image can be used to reduce the dimensions of the SPECT reconstruction by limiting the computation to the smaller FOV while reducing artifacts resulting from the truncated data. Since SPECT imaging within a LFOV is used, it is defined for the purposes of this specification as a keyhole SPECT (K-SPECT) method. Image reconstruction is performed in a computer or data processor well known to the art and conventionally used in or in combination with MRI or nuclear imaging systems. The output of the computer may be a hardcopy image or a digital image that is stored, displayed and/or transmitted by any kind by any kind of conventional digital storage, display or transmission device.

At first MRI images of the entire object or biological specimen using a larger FOV are obtained to determine the location of the ROI covering the target organ. Once the ROI is determined, the object is moved inside the radiofrequency (RF) coil of the MRI/SPECT scanner to bring the target area inside the LFOV and then simultaneously, or at least near simultaneous or coregistered MRI and SPECT is performed. It will be understood that whenever the term "simultaneous" is used includes temporal coincidence, but in general at least substantial spatial coregistration of the object during MR and SPECT imaging. By "substantial spatial coregistration" it is meant that the object's position does not change enough between the MR and SPECT imaging steps that any effect of misrepresentation arises which interferes with the practical utilization of the image in the present context.

The spatial resolution of the SPECT image is improved by employing a pinhole collimator with magnification greater than 1 by having carefully calculated acceptance angles for each pinhole to avoid multiplexing. All the pinholes are focused to the center of the LFOV.

K-SPECT reconstruction is accomplished by generating an adaptive weighting matrix using a priori information obtained by simultaneously acquired MR images and the radioactivity distribution obtained from the ROI region of the SPECT image that is reconstructed without any a priori input.

Preliminary results using simulations with numerical phantoms show that the image resolution of the SPECT image within the LFOV is improved while minimizing artifacts arising from parts of the object outside the LFOV due to the chosen magnification and the new reconstruction technique. The root-mean-square-error (RMSE) in the out-of-field artifacts was reduced by 60% for spherical phantoms using the K-SPECT reconstruction technique and by 48.5-52.6% for the heart in the case with the MOBY phantom. Keyhole SPECT reconstruction technique significantly improves the spatial resolution and quantification while reducing artifacts from the contributions outside the LFOV as well as reducing the dimension of the reconstruction matrix.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The specification contains at least one drawing executed in color. Copies of this patent or patent application publication with color drawing(s) will be provided by the Office upon request and payment of the necessary fee.

FIG. 3c is a reconstructed data image of the phantom of FIG. 3a using the standard ML-EM method with no a priori data employed to render the image.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

A combined MRI/SPECT system can be used to choose a region of interest (ROI) 10 in an animal or patient for SPECT imaging. It must be understood that any nuclear imaging technique can be substituted for SPECT, namely positron emission tomography (PET) imaging can also be used as a combined modality. Therefore, wherever SPECT is referenced it must be understood to include all nuclear imaging techniques, including without limitation PET.

Figure 1A:
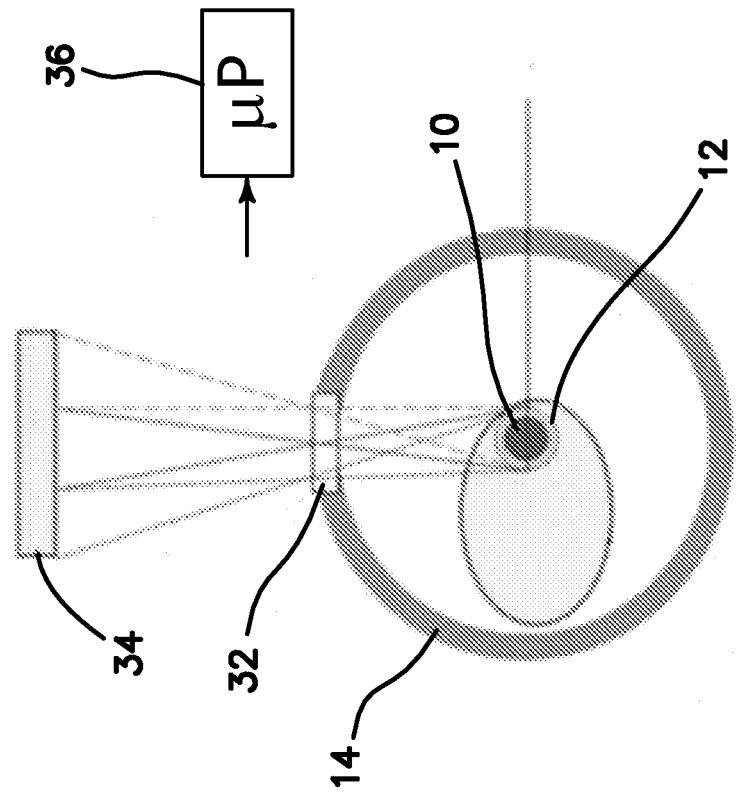
FIG. 1a shows an animal body (the ellipse) set at the center of the RF coil, but the ROI is outside of the LFOV seen by the nuclear detector.
Figure 1B:
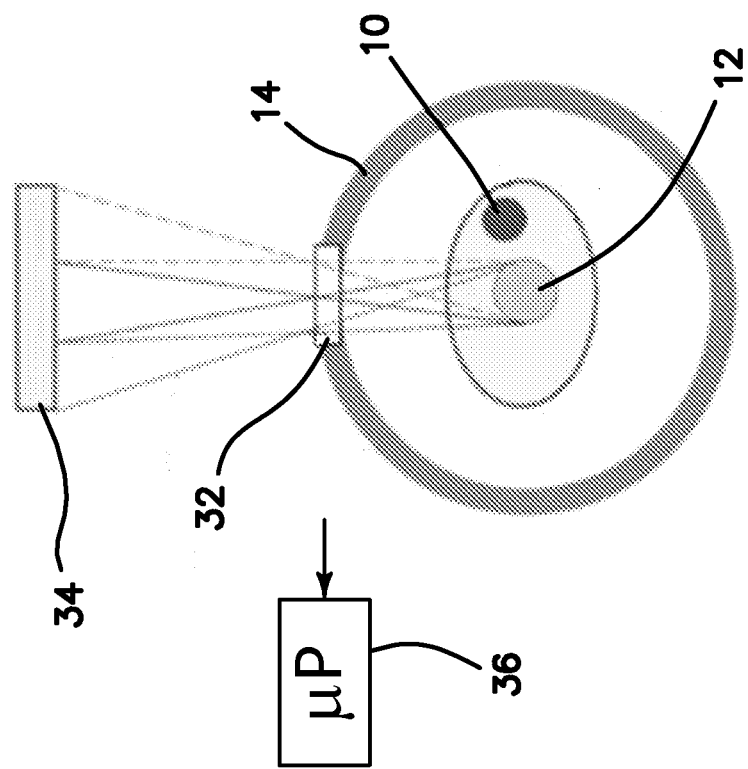
In FIG. 1b the animal is moved to the left in the view of the drawing in order for the ROI's center to coincide with the center of the LFOV. The dimensions shown in the figure are the actual values used in the simulation studies.

At first the ROI 10 that covers the target organ needs to be determined from the MR images. This is done by performing a whole-body MRI or at least a wide field of view scan and then selecting a three dimensional spherical volume of interest (VOI) from these images to cover the target region. Once the VOI is determined from the MRI images, the animal or patient bed can be moved to position the VOI at the center of the LFOV 12 of the detector system as shown in FIG. 1b. With the ROI 10 determined, the animal or patient is moved inside the radiofrequency (RF) coil 14 of the MRI subsystem (not shown) to bring the target area inside the LFOV 12 and then simultaneous MRI and SPECT are performed. The spatial resolution of the SPECT image obtained by CZT detector 34 is improved by employing a pinhole collimator 32 described above. Except as modified as disclosed herein for the purpose of combined multimodality, the hardware and operational data acquisition of the MRI and SPECT subsystems are conventional and will not be further described in detail, since their separate elements and operation is well known.

K-SPECT reconstruction is performed in computer 36 by generating an adaptive weighting matrix using a priori information obtained by simultaneously acquired MR images and the radioactivity distribution obtained from the ROI region 10 of the SPECT image that is reconstructed without any a priori input. Results using simulations with numerical phantoms show that the image resolution of the SPECT image within the LFOV 12 is improved while minimizing artifacts arising from parts of the object outside the LFOV 12 due to the chosen magnification and the new reconstruction technique.

The central trans-axial slice is through the volume of interest (VOI), which will be indicated as the ROI 10. After this re-alignment process from the view of FIG. 1a to that of FIG. 1b, the object remains at the same position so that the center of rotation within the object remains the same during the entire simultaneous MRI/SPECT image acquisition. The circular ROI 10 includes both the target organ as well as the surrounding background within the LFOV 12.

Since the images from MRI and SPECT are very different in content, image coregistration by software leads to image distortions, which is a typical problem for the post-image-processing methods even when markers are used. However, with the combined MRI/SPECT imaging system, the image coregistration by software is not necessary because the two scanners are mechanically or spatially fully coregistered and remain so while all the images are acquired simultaneously.

Although the signal intensity distribution in MRI is different from that in the SPECT image due to the different physical and biological origins for each signal, MRI can still provide a high-resolution anatomical image of the target region. Once the ROI 10 is determined from the MR image, it can be used to form a template to separate the target and non-target regions in the SPECT image reconstruction. The average counts in the target and background regions are calculated from the initial SPECT image. Then each pixel of the template covering the target organ generated by the MR image is assigned the same average target-to-background (T/B) value while the pixels outside the target organ, but within the LFOV 12, are assigned a value of 1. Finally, the pixels outside the LFOV 12 are given a value of 0. This weighting factor map is then used to modify the system matrix to take into account the average emission probability from each pixel using the MR and initial SPECT images. If one wishes to make the mapping more complicated, a different weighting map that takes into account pixel by pixel variations of the emission probability can also be generated. In our simulation studies we did not take the effects of attenuation into account. As is well known, MRI information could also be used to perform the necessary attenuation correction.

In order to reject the contributions from outside the LFOV 12 and take into account the emission probabilities within the LFOV 12, it is necessary to generate a weighting map so that only voxels inside the LFOV 12 contribute during the reconstruction process. Equations (1) and (2) show how the a priori information from the reconstructed image using SPECT without a priori information and the anatomical information from MRI are used to generate the adaptive system matrix, $S'_{i,j}$:

$$S'_{i,j} = \sum_k S_{i,k} \xi_{k,j} \qquad (1)$$

where $$\xi_{k,j} = \begin{cases} T/B & \text{if} \quad (k,j) \in \text{target} \\ 1 & \text{if} \quad (k,j) \in LFOV \cap \text{target}^c \\ 0 & \text{if} \quad (k,j) \in LFOV^c \end{cases} \qquad (2)$$

Where $S_{i,j}$ is the system matrix, and where the elements of the weighting matrix, $\xi_{k,j}$, within the LFOV 12 given in equation (2) are calculated as described above, where target$^c$ is a region outside the target region and where LFOV$^c$ is a region outside the LFOV. All the a priori information obtained from the MRI and the initial SPECT image is included in this weighting matrix that is nothing but an 'un-normalized' probability distribution matrix. It should be emphasized that a new weighting matrix needs to be generated only once during the image reconstruction procedure for a given object. 'LFOV$^c$' in equation (2) indicates that the voxels do not belong to the LFOV 12, and 'target' in equation (2) indicates that the voxels do not belong to the ROI 10 (target).

With the modified system matrix $S'_{i,j}$ for the LFOV 12, the image reconstruction is performed using the Maximum Likelihood Estimation—Expectation Maximization (ML-EM) algorithm shown in equation (4) below with equations (1) and (2) above. In this disclosure, this method using the adaptive sensitivity matrix (equation (4)) will be called the K-SPECT method to distinguish it from standard reconstruction using the ML-EM algorithm with the detection probability matrix given in equation (3) where no a priori information is used, namely $$S'_{i,j} = S_{i,j}. \qquad (3)$$

$$\lambda_j^{n+1} = \frac{\lambda_j^n}{\sum_m S'_{m,j}} \sum_i S'_{i,j} \frac{Q_i}{\sum_k S'_{i,k}\lambda_k^n}. \qquad (4)$$

Where $\lambda_{n+1,j}$ is the reconstructed value for voxel j at $(n+1)^{th}$ iteration and $Q_i$ is the measured value for projection i.

The simulation results presented below in connection with FIGS. 4a-4d show that incorporation of a priori information results in the improvement of the SPECT images by reducing the artifacts arising from radioactivity outside the LFOV 12 when compared to SPECT images that do not use any a priori information during reconstruction.

It is important to align the centers of the ROI 10 and LFOV 12 with the rotation axis accurately. The LFOV 12 used here was 10 mm in diameter. The alignment of the ROI 10 at the center of the imaging space reduces the chance of a part of the object of interest to be left outside the LFOV 12 or inclusion of an object of no interest within the LFOV 12.

In order to compare the reconstructed image ($I_r$) with the actual image ($I_a$-data from the phantom), the errors were evaluated using the root-mean-square-error (RMSE) criterion given by $$\varepsilon^2 = \frac{\sum_{n=1}^{N} [I_a - I_r]^2}{\sum_{n=1}^{N} [I_a]^2} \qquad (5)$$

(N, the number of voxels).

where $I_a$ and $I_r$ are defined above.

Attenuation can be corrected using an attenuation map that can be obtained from the segmented MR image. Scatter on the other hand could be corrected by using the well-known three-energy-window technique commonly used in clinical SPECT. In the present approach the object can be sampled adequately within the axial direction by rotating the detectors around the longitudinal axis, but the data in the azimuthal direction are not fully sampled for cone beam geometry. However, the azimuthal sampling can be improved by moving the patient bed in steps similar to spiral scanning in CT.

Figure 2:
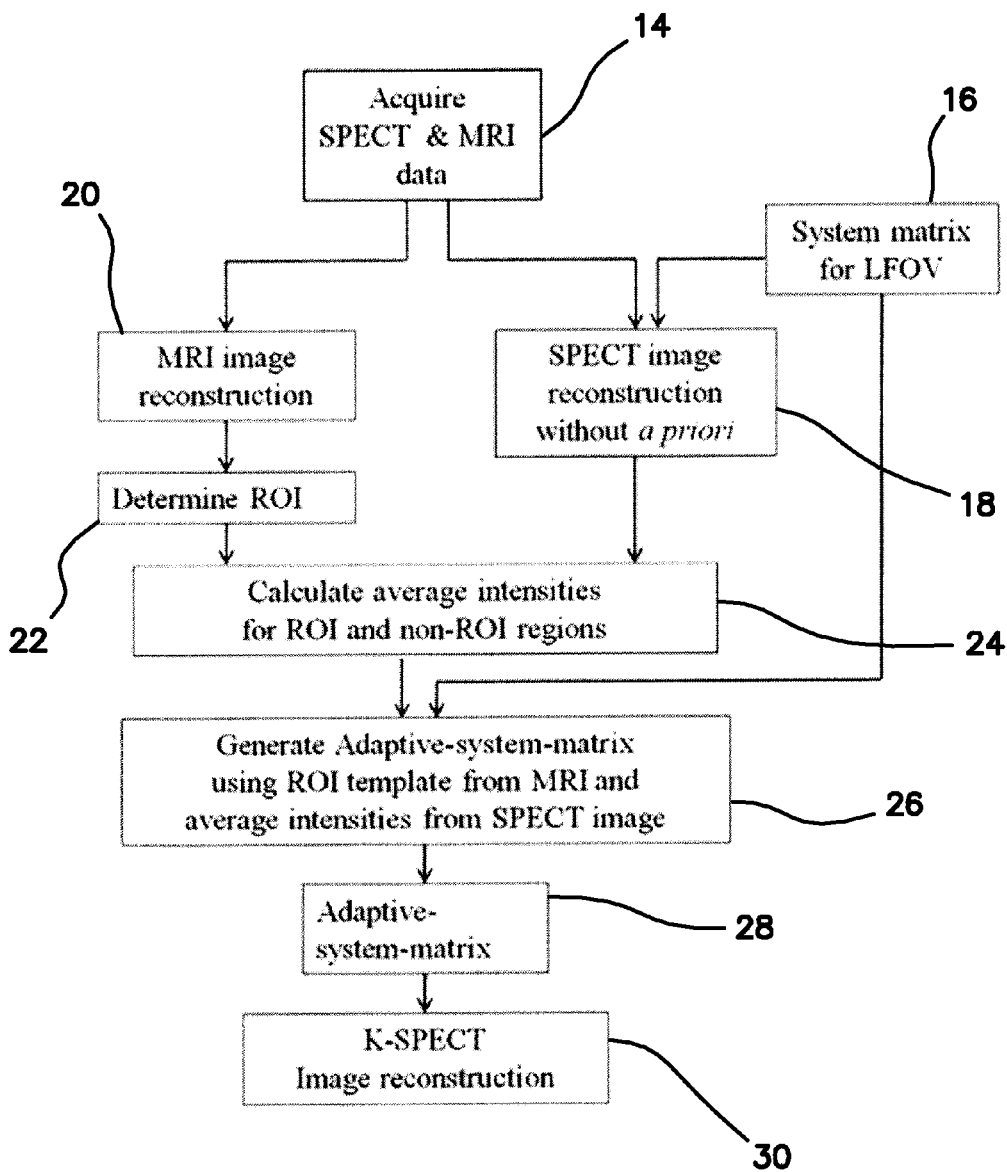
FIG. 2 is a flow that diagrams the reconstruction of the MRI and SPECT images according to the invention.

The process is summarized in the flow diagram of FIG. 2. SPECT and MRI data is acquired for the aligned ROI 10 and LFOV 12 in step 14. Using the system matrix information in the LFOV 12 at step 16 and the SPECT data, the SPECT image without a priori information is reconstructed at step 18 and the MRI image is reconstructed from the MRI data at step 20. From the MRI image the ROI 10 is determined at step 22. The average intensities of the ROI and non-ROI regions for both the MRI and SPECT images are calculated at step 24. Again using the system matrix information for the LFOV 12 from step 16 and the results of step 24 the adaptive system matrix using the ROI template from the MRI and average intensities from the SPECT image are generated at step 26. An adaptive system matrix is then defined at step 28 and the K-SPECT image reconstruction according to the invention may be completed at step 30.

Figure 3A:
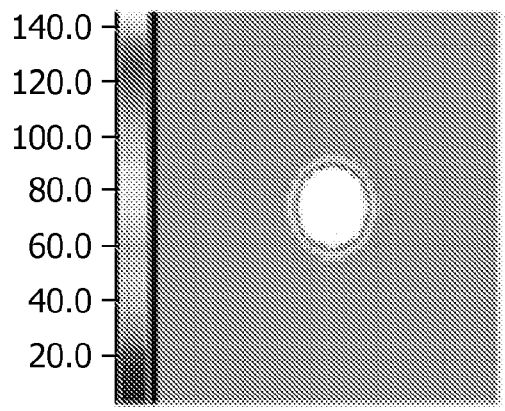
FIG. 3a is a diagram of a spherical phantom (8 mm in diameter) with 5:1 contrast.
Figure 3B:
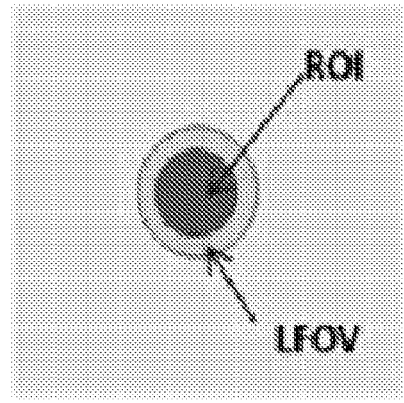
FIG. 3b is illustrative depiction of the ROI (8 mm in diameter) within the LFOV (10 mm in diameter).
Figure 3C:
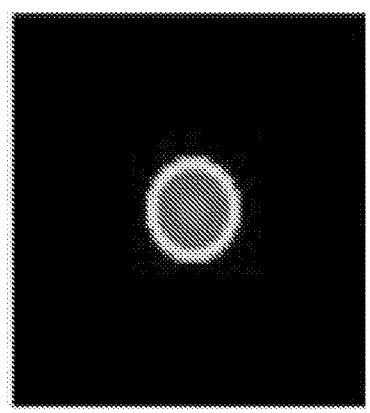
FIG. 3c is a reconstructed data image of the phantom of FIG. 3a using the K-SPECT method of the illustrated embodiment.
Figure 3D:
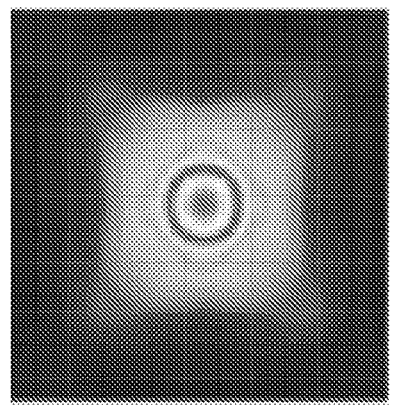

With the current described method of this invention, FIGS. 3a-3d show in FIG. 3b the reconstruction of a image. FIG. 3c shows the image using current ML-EL reconstruction method while FIG. 3a is the resolution phantom. FIG. 3d shows how accurate the current technique is at reproducing the image of the resolution phantom when compared to the current ML-EL reconstruction method.

Figure 4A:
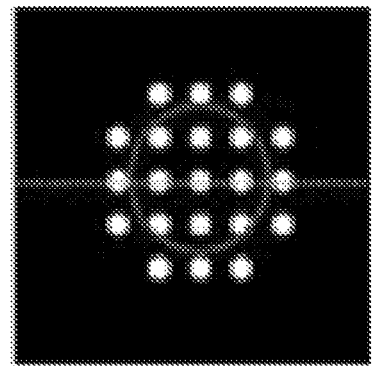
FIG. 4a is a two dimensional data graph of a resolution phantom.
Figure 4B:
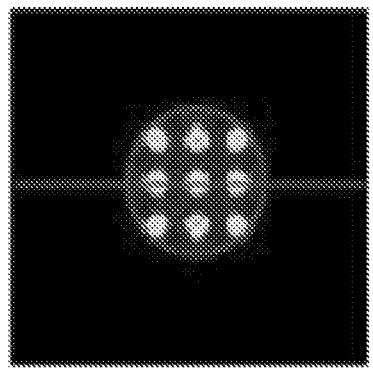
FIG. 4b is a reconstructed data image using the K-SPECT technique of the illustrated embodiment.
Figure 4C:
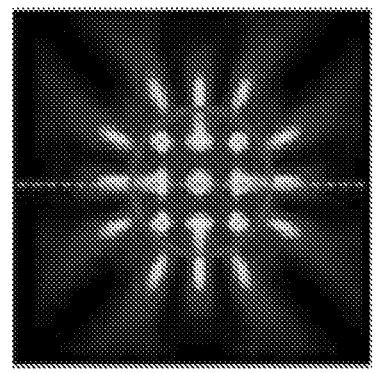
FIG. 4c is a reconstructed data image using the standard ML-EM method that does not use any a priori information.
Figure 4D:
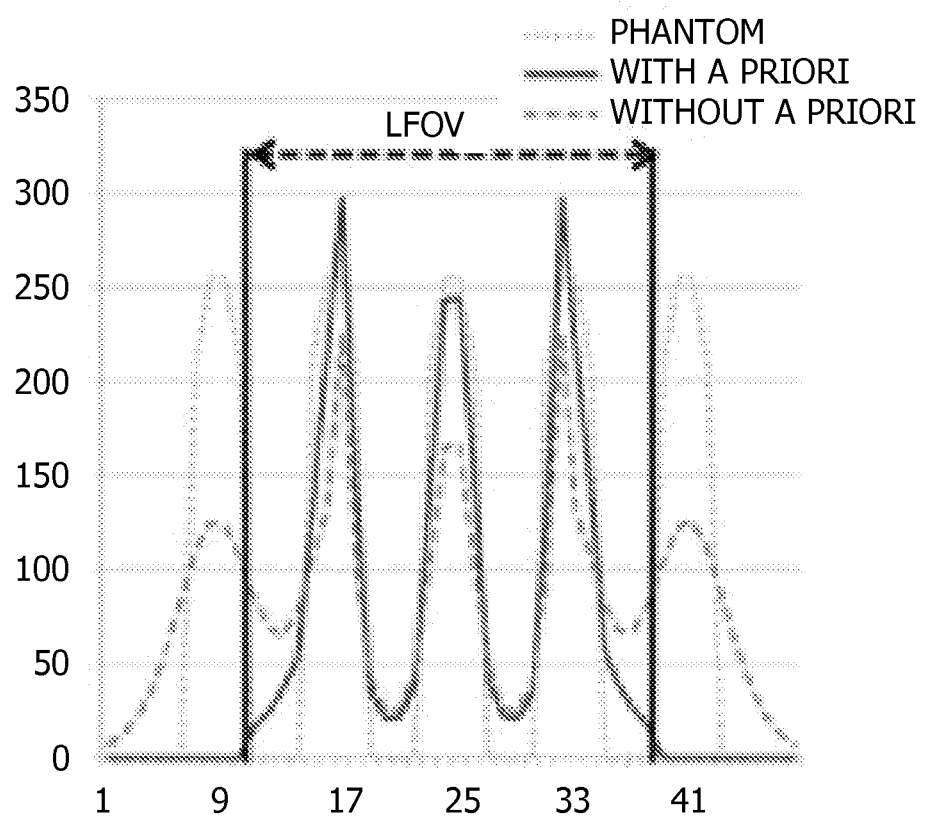
FIG. 4d is a graph of the intensity profiles measured through a horizontal midline through all three data images of FIGS. 4a-4c.

Consider the effects of out-of-field objects on the resolution phantom. The resolution phantom was reconstructed by using both techniques with a LFOV 12 of 10 mm in diameter. The LFOV 12 is overlaid over the phantom and reconstructed images in FIGS. 4a-4d in red to indicate its position. In this case we assumed no background signal. FIG. 4a is an image of the resolution phantom and FIG. 4b shows the reconstructed image using the K-SPECT technique of the illustrated embodiment. FIG. 4c is the reconstructed image using the standard ML-EM method that does not use any a priori information. FIG. 4d is a graph of horizontal intensity profiles through all three images of FIGS. 4a-4b. In case of FIG. 4c the reconstruction was performed over the entire reconstruction area in contrast to FIG. 4b where it was only performed within the LFOV 12. The intensity profiles shown in FIG. 4d indicate that the K-SPECT profile is very close to the actual profile obtained from the phantom whereas the profile obtained using reconstruction without the a priori underestimates the signal intensities considerably within the LFOV 12 (between two black solid lines).

Thus, in summary the illustrated embodiments include a method of improving the resolution of SPECT imaging of a target region of a biological object comprising the steps of simultaneously performing MRI and SPECT imaging to identify a limited field of view (LFOV) which includes a region of interest; generating average intensities for the region of interest and a region outside the region-of-interest; generating an adaptive system matrix defined by $$S'_{i,j} = \sum_k S_{i,k} \xi_{k,j} \quad (1)$$

where $$\xi_{k,j} = \begin{cases} T/B & \text{if} \quad (k, j) \in \text{target} \\ 1 & \text{if} \quad (k, j) \in LFOV \cap \text{target}^c \\ 0 & \text{if} \quad (k, j) \in LFOV^c \end{cases} \quad (2)$$

where $S_{i,j}$ is the system matrix, and where the elements of the weighting matrix, $\xi_{k,j}$, within the LFOV, where $\text{target}^c$ is a region outside the target region and where $LFOV^c$ is a region outside the LFOV; and generating an image of the region of interest in the LFOV using the adaptive system matrix.

The illustrated embodiments can also be defined as a method for obtaining a high-resolution nuclear image of a biological object, which image is acquired by a nuclear detector inside an MRI system comprising the steps of acquiring MRI information pertaining to a wide field of view; focusing a field of view of the nuclear detector to a small region that covers only the target region; obtaining a nuclear image of the small region; and using a priori information included in the MRI information to eliminate image artifacts in the nuclear image.

In one embodiment the nuclear image is a PET or SPECT image.

In still another embodiment the biological object to be imaged is larger than a predefined limited field of view (LFOV) and where a region of interest of the biological object is moved into the LFOV using the MRI information to identify coordinates of the region of interest so that the region of interest can be moved into the LFOV, after which the nuclear detector is focused on a small region that covers only the target region and the nuclear image of the small region is obtained.

The step of obtaining a nuclear image comprises using a multimodality MR/SPECT system to obtain simultaneous MRI and SPECT images to eliminate misregistration between MR images used as a priori information for SPECT imaging in a limited-field-of-view (LFOV) and performing SPECT reconstruction of the image in the LFLOV using MR images as a priori information.

The method may further comprise the step of using a multiple pinhole collimator for nuclear imaging and focusing all pinholes on a center of the LFOV.

The step of performing SPECT reconstruction comprises generating an adaptive weighting matrix using a priori information obtained from simultaneously acquired MR images and using radioactivity distribution obtained from the region of interest in the SPECT image reconstructed without any a priori input.

The step of using a priori information included in the MRI information to eliminate image artifacts in the nuclear image comprises using the MRI information to form a template to separate the target and non-target regions in the SPECT image reconstruction.

In one embodiment the step of using the MRI information to form a template comprises determining an average count in the region of interest and in the LFOV outside the region of interest from an initial SPECT image, assigning each pixel of the template in the region of interest pixel by pixel variations of the emission probability while assigning each pixel outside the region of interest a value of 1, assigning each pixel outside the LFOV a value of 0 to provide a weighting factor map as determined by the template, and modifying a system matrix to take into account the average emission probability from each pixel using the MR image and initial SPECT image.

The step of using the MRI information to form a template comprises assigning each pixel of the template in the region of interest a pixel-by-pixel value equal to an emission probability for the location of the assigned pixel, while assigning each pixel outside the region of interest a value of 1, assigning each pixel outside the LFOV a value of 0 to provide a weighting factor map as determined by the template, and modifying a system matrix to take into account the average emission probability from each pixel using the MR image and initial SPECT image.

The step of using the MRI information to form a template to separate the target and non-target regions in the SPECT image reconstruction comprises generating a weighting map so that only voxels inside the LFOV contribute during the reconstruction process.

The step of using a priori information included in the MRI information to eliminate image artifacts in the nuclear image comprises using a modified system matrix $S'_{i,j}$ for the LFOV, and performing image reconstruction using a maximum likelihood estimation—expectation maximization (ML-EM) algorithm.

The illustrated embodiments also include an apparatus for obtaining a high-resolution nuclear image of a biological object according to any one of the above methods. For example, an apparatus comprising an MRI subsystem having a wide field of view; a nuclear imaging subsystem having a limited field of view (LFOV); means for moving a biological object having a region of interest (ROI) into the LFOV using wide field of view MRI information, such as a three dimensional linear translational stage; a nuclear detector included in the nuclear imaging subsystem focused on a small region that covers only region of interest; and a computer communicated to the MRI and nuclear imaging subsystems for reconstructing a nuclear image of the small region acquired by the nuclear detector using a priori MRI information to eliminate image artifacts in the reconstructed nuclear image.

The nuclear imaging subsystem may comprise a SPECT or a PET subsystem.

The illustrated embodiments also include within their scope imaging data recorded on a tangible medium or in a memory generated by a computer in an apparatus for obtaining a high-resolution nuclear image of a biological object according to any one of the above methods or apparatus.

Many alterations and modifications may be made by those having ordinary skill in the art without departing from the spirit and scope of the embodiments. Therefore, it must be understood that the illustrated embodiment has been set forth only for the purposes of example and that it should not be, taken as limiting the embodiments as defined by the following embodiments and its various embodiments.

Therefore, it must be understood that the illustrated embodiment has been set forth only for the purposes of example and that it should not be taken as limiting the embodiments as defined by the following claims. The illustrated embodiment has been described in the context of a small animal imagining system or for imaging an organ, but it is to be expressly understood that it is within the spirit and scope of the invention to utilize the apparatus and method for general human as well animal use in partial or whole body examinations or any other biological specimen.

For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. Method of improving the resolution of SPECT imaging of a region of interest of a biological object comprising:
performing a first MRI scan on a biological object to determine a limited field of view (LFOV);
moving the region of interest into the LFOV of an MRI imaging system and SPECT imaging system based on the first MRI scan;
simultaneously performing a second MRI and first SPECT scan on the LFOV to acquire second MRI data and first SPECT data;
generating an adaptive system matrix using average intensities generated from the second MRI and first SPECT data, wherein the adaptive system matrix is defined by $$S'_{i,j} = \sum_k S_{i,k} \xi_{k,j} \quad (1)$$

where $$\xi_{k,j} = \begin{cases} T/B & \text{if} \quad (k,j) \in \text{target} \\ 1 & \text{if} \quad (k,j) \in LFOV \cap \text{target}^C \\ 0 & \text{if} \quad (k,j) \in LFOV^C \end{cases} \quad (2)$$

where $S_{i,j}$ is the system matrix, where T/B is the target-to-background value, where $\xi_{k,j}$ is the elements of the weighting matrix within the LFOV, where target$^C$ is a region outside the target region and where LFOV$^C$ is a region outside the LFOV; and
generating an image of the region of interest in the LFOV using the adaptive system matrix.

2. The method of claim 1, further comprising using a multiple pinhole collimator for obtaining the first SPECT data and focusing all pinholes on a center of the region of interest.

3. The method of claim 1, wherein generating an image of the region of interest comprises performing image reconstruction by forming a template to separate the region of interest, non-regions of interest inside the limited field of view, and regions outside the limited field of view.

4. The method of claim 1, wherein the SPECT imaging system is a keyhole SPECT imaging system.

5. The method of claim 1, further comprising outputting the image of the region of interest.

6. The method of claim 1, further comprising storing the image of the region of interest.

7. The method of claim 1, wherein the MRI imaging system and SPECT imaging system are mechanically or spatially fully coregistered.

8. An apparatus for obtaining an image of a biological object, the apparatus comprising:

an MRI system, the MRI system configured to perform a first MRI scan on a biological object to determine a limited field of view (LFOV);

a SPECT system;

a means for moving a region of interest of the biological object into the LFOV;

a nuclear detector included in the SPECT system focused on the region of interest, wherein the MRI system and SPECT system are configured to simultaneously perform a second MRI scan and a first SPECT scan on the LFOV to acquire second MRI data and first SPECT data; and a computer configured to:
generate an adaptive system matrix using average intensities generated from the second MRI and first SPECT data, wherein the adaptive system matrix is defined by $$S'_{i,j} = \sum_k S_{i,k} \xi_{k,j} \quad (1)$$

where $$\xi_{k,j} = \begin{cases} T/B & \text{if} \quad (k, j) \in \text{target} \\ 1 & \text{if} \quad (k, j) \in LFOV \cap \text{target}^C \ldots \\ 0 & \text{if} \quad (k, j) \in LFOV^C \end{cases} \quad (2)$$

where $S_{i,j}$ is the system matrix, where T/B is the target-to-background value, where $\xi_{k,j}$ is the elements of the weighting matrix within the LFOV, where $\text{target}^C$ is a region outside the target region and where $LFOV^C$ is a region outside the LFOV; and generate an image of the region of interest in the LFOV using the adaptive system matrix.

9. The apparatus of claim 8, wherein the SPECT system is a keyhole SPECT imaging system.

10. The apparatus of claim 8, wherein the computer is configured to output the image of the region of interest.

11. The apparatus of claim 8, wherein the computer is configured to store the image of the region of interest.

12. The apparatus of claim 8, wherein the MRI system and SPECT system are mechanically or spatially fully coregistered.

13. An apparatus for obtaining an image of a biological object, the apparatus comprising:
an MRI system, the MRI system configured to perform a first MRI scan on a biological object to determine a limited field of view (LFOV);
a nuclear imaging system;
a means for moving a region of interest of the biological object into the LFOV;
a nuclear detector included in the nuclear imaging system focused on the region of interest, wherein the MRI system and nuclear imaging system are configured to simultaneously perform a second MRI scan and a first nuclear imaging scan on the LFOV to acquire second MRI data and first nuclear imaging data; and
a computer configured to:
generate an adaptive system matrix using average intensities generated from the second MRI and first nuclear imaging data, wherein the adaptive system matrix is defined by $$S'_{i,j} = \sum_k S_{i,k} \xi_{k,j} \quad (1)$$

where $$\xi_{k,j} = \begin{cases} T/B & \text{if} \quad (k, j) \in \text{target} \\ 1 & \text{if} \quad (k, j) \in LFOV \cap \text{target}^C \ldots \\ 0 & \text{if} \quad (k, j) \in LFOV^C \end{cases} \quad (2)$$

where $S_{i,j}$ is the system matrix, where T/B is the target-to-background value, where $\xi_{k,j}$ is the elements of the weighting matrix within the LFOV, where $\text{target}^C$ is a region outside the target region and where $LFOV^C$ is a region outside the LFOV; and generate an image of the region of interest in the LFOV using the adaptive system matrix.

14. The apparatus of claim 13, wherein the nuclear imaging system is selected from a SPECT system or a PET system.

15. Method of improving the resolution of nuclear imaging of a region of interest of a biological object comprising:
performing a first MRI scan on a biological object to determine a limited field of view (LFOV);
moving the region of interest into the LFOV of an MRI system and nuclear imaging system based on the first MRI scan;
simultaneously performing a second MRI and first nuclear imaging scan on the LFOV to acquire second MRI data and first nuclear imaging data;
generating an adaptive system matrix using average intensities generated from the second MRI and first nuclear imaging data, wherein the adaptive system matrix is defined by $$S'_{i,j} = \sum_k S_{i,k} \xi_{k,j} \quad (1)$$

where $$\xi_{k,j} = \begin{cases} T/B & \text{if} \quad (k, j) \in \text{target} \\ 1 & \text{if} \quad (k, j) \in LFOV \cap \text{target}^C \ldots \\ 0 & \text{if} \quad (k, j) \in LFOV^C \end{cases} \quad (2)$$

where $S_{i,j}$ is the system matrix, where T/B is the target-to-background value, where $\xi_{k,j}$ is the elements of the weighting matrix within the LFOV, where $\text{target}^C$ is a region outside the target region and where $LFOV^C$ is a region outside the LFOV; and
generating an image of the region of interest in the LFOV using the adaptive system matrix.

16. The method of claim 15, wherein the nuclear imaging system is selected from a SPECT system or a PET system.

* * * * *